(12) United States Patent
Jiang et al.

(10) Patent No.: US 11,512,841 B1
(45) Date of Patent: Nov. 29, 2022

(54) AUTOMATICALLY ADJUSTABLE SHADOWLESS OPERATING LAMP

(71) Applicant: Taizhou People's Hospital, Taizhou (CN)

(72) Inventors: Jianxin Jiang, Taizhou (CN); Aiqin Gu, Taizhou (CN); Jun Lu, Taizhou (CN); Wei Ling, Taizhou (CN); Xiaolin Wang, Taizhou (CN); Xiaohong Zhang, Taizhou (CN); Zhenqing Ren, Taizhou (CN); Guangzhong Gao, Taizhou (CN); Yasuo Ding, Taizhou (CN)

(73) Assignee: Taizhou People's Hospital, Taizhou (CN)

( * ) Notice: Subject to any disclaimer, the term of this patent is extended or adjusted under 35 U.S.C. 154(b) by 0 days.

(21) Appl. No.: 17/844,938

(22) Filed: Jun. 21, 2022

(30) Foreign Application Priority Data

Jun. 21, 2021 (CN) .......................... 202110684470.4

(51) Int. Cl.
*F21V 21/15* (2006.01)
*F21V 21/22* (2006.01)
(Continued)

(52) U.S. Cl.
CPC .............. *F21V 21/15* (2013.01); *F21V 21/03* (2013.01); *F21V 21/22* (2013.01); *F21V 21/29* (2013.01);
(Continued)

(58) Field of Classification Search
CPC ... F21W 2131/205; F21V 21/14; F21V 21/15; F21V 21/22; F21V 21/26; F21V 21/28;
(Continued)

(56) References Cited

U.S. PATENT DOCUMENTS 6,416,207 B1 * 7/2002 Chang ..................... F21V 21/26
362/418
2002/0139913 A1 * 10/2002 Kummerfeld ........... F21V 21/26
248/343
(Continued)

FOREIGN PATENT DOCUMENTS

CN 201248169 Y 5/2009
CN 101858537 A 10/2010
(Continued)

OTHER PUBLICATIONS

First Office Action issued in counterpart Chinese Patent Application No. 202110684470.4, dated Oct. 22, 2021.
(Continued)

*Primary Examiner* — Colin J Cattanach
(74) *Attorney, Agent, or Firm* — Westbridge IP LLC

(57) ABSTRACT

Disclosed is an automatically adjustable shadowless operating lamp. The automatically adjustable shadowless operating lamp comprises a telescopic support rod. The telescopic support rod is rotatably connected with a first lighting assembly and a second lighting assembly with a same structure, the second lighting assembly is positioned above the first lighting assembly, and the second lighting assembly moves independently with the first lighting assembly; the first lighting assembly comprises a first adjusting part, the first adjusting part is rotationally connected with the telescopic support rod, and is hinged with an adjusting rod through an adjusting piece, a tail end of the adjusting rod is fixedly connected with a second adjusting part, and the adjusting rod is hinged with an operating lamp through the second adjusting part.

6 Claims, 9 Drawing Sheets

(51) Int. Cl.
*F21V 23/04* (2006.01)
*F21V 21/03* (2006.01)
*F21V 21/29* (2006.01)
*F21W 131/205* (2006.01)
*F21V 21/14* (2006.01)
*F21V 14/02* (2006.01)
*F21V 21/32* (2006.01)
*F21V 21/28* (2006.01)
*A61B 90/35* (2016.01)
*F21V 21/26* (2006.01)
*A61B 90/30* (2016.01)
*F21V 21/30* (2006.01)

(52) U.S. Cl.
CPC .......... *F21V 23/0435* (2013.01); *A61B 90/30* (2016.02); *A61B 90/35* (2016.02); *F21V 14/02* (2013.01); *F21V 21/14* (2013.01); *F21V 21/26* (2013.01); *F21V 21/28* (2013.01); *F21V 21/30* (2013.01); *F21V 21/32* (2013.01); *F21V 23/045* (2013.01); *F21W 2131/205* (2013.01)

(58) Field of Classification Search
CPC ...... F21V 21/29; F21V 21/30; F21V 23/0435; F21V 14/02; F21V 23/32; F21V 23/045; A61B 90/30; A61B 90/308; A61B 90/309; A61B 90/35
See application file for complete search history.

(56) References Cited

U.S. PATENT DOCUMENTS

| | | | | |
|---|---|---|---|---|
| 2011/0079697 | A1* | 4/2011 | Muller | F16M 11/2064 |
| | | | | 248/323 |
| 2019/0249847 | A1* | 8/2019 | Hallack | F21V 23/0442 |
| 2020/0306006 | A1* | 10/2020 | Bellows | A61B 90/50 |
| 2021/0302808 | A1* | 9/2021 | Watson | G03B 15/14 |

FOREIGN PATENT DOCUMENTS

| | | | | |
|---|---|---|---|---|
| CN | 205535326 U | | 8/2016 | |
| CN | 106813170 A | | 6/2017 | |
| CN | 112393166 A | * | 2/2021 | |
| CN | 112815252 A | * | 5/2021 | ............. F21S 8/033 |
| CN | 112879879 A | * | 6/2021 | |
| JP | 2002510135 A | | 4/2002 | |

OTHER PUBLICATIONS

Second Office Action issued in counterpart Chinese Patent Application No. 202110684470.4, dated Jan. 14, 2022.

* cited by examiner

AUTOMATICALLY ADJUSTABLE SHADOWLESS OPERATING LAMP

CROSS-REFERENCE TO RELATED APPLICATIONS

This present disclosure claims priority to Chinese Patent Application 202110684470.4, filed on Jun. 21, 2021, the contents of which are hereby incorporated by reference.

TECHNICAL FIELD

The present disclosure relates to the technical field of operating instruments, and in particular to an automatically adjustable shadowless operating lamp.

BACKGROUND

At present, most of shadowless lamps used in clinic are ceiling-mounted and mechanically adjusted, and there will be following problems in use. Firstly, due to the complex structure and mostly mechanical connection of shadowless lamps, the flexibility of joints decreases after a long time of use, which makes the adjusted shadowless lamps easy to move. Secondly, when the surgeon raises his hand to adjust an angle of the light, the hand is out of the sterile area, increasing the possibility of contamination. Thirdly, during use, the doctor can't control the brightness of the operating lamp according to the operation situation. Lastly, for some operations with a small field of vision, the operating lamp can't be precisely adjusted or illuminate precisely. Therefore, there is an urgent need for a shadowless operating lamp with a simple structure and convenient use, which can reduce the contamination probability in the adjustment process.

SUMMARY

The objective of the present disclosure is to provide an automatically adjustable shadowless operating lamp, so as to solve the above problems existing in the prior art, optimize the mechanical structure of the original operating lamp, and automatically adjust the position, brightness and distance of the operating lamp. This device could use an intraoperative adjuster to make the shadowless operating lamp inject light in the specified direction according to the requirements of the operator, and could also use a pedal adjuster to adjust the distance between the shadowless lamp and the operating area and the illumination brightness of the shadowless lamp according to the requirements.

In order to achieve the above objective, the present disclosure provides the following scheme: the present disclosure provides an automatically adjustable shadowless operating lamp, which comprises a telescopic support rod, wherein the telescopic support rod is rotatably connected with a first lighting assembly and a second lighting assembly with a same structure, the second lighting assembly is positioned above the first lighting assembly, and the second lighting assembly moves independently with the first lighting assembly; the first lighting assembly comprises a first adjusting part, the first adjusting part is rotationally connected with the telescopic support rod and is hinged with an adjusting rod through an adjusting piece, and a tail end of the adjusting rod is fixedly connected with a second adjusting part, and the adjusting rod is hinged with an operating lamp through the second adjusting part, and the operating lamp is electrically connected with a brightness adjuster arranged below an operating table; a first infrared sensor is arranged at a bottom of the operating lamp, a second infrared sensor is arranged in the operating lamp, and the first infrared sensor, the second infrared sensor, the first adjusting part, the adjusting rod and the adjusting piece are all electrically connected with an intraoperative adjuster arranged on the operating table.

Optionally, the first adjusting part comprises a rotary motor arranged in the telescopic support rod, which is electrically connected with the intraoperative adjuster, an output end of the rotary motor is fixedly connected with a connecting rod, and the telescopic support rod is externally sleeved with a swivel hinged with the adjusting rod, and the swivel is fixedly connected with the connecting rod through a bearing.

Optionally, the adjusting rod comprises a sleeve hinged with the swivel, a first hydraulic pump and a long rod are arranged in the sleeve, the first hydraulic pump is electrically connected with the intraoperative adjuster, the long rod is telescoped in the sleeve through the first hydraulic pump, a tail end of the long rod is fixedly connected with a ball, and a bottom end of the operating lamp is fixedly connected with a ball seat which is matched with the ball.

Optionally, the second adjusting part comprises a supporting plate fixedly connected with the long rod, and a plurality of second hydraulic pumps are circumferentially fixedly connected to one side of the supporting plate close to the operating lamp, and all the second hydraulic pumps are electrically connected with the intraoperative adjuster, and movable ends of the second hydraulic pumps are fixedly connected with the ball seat through nitinol wires.

Optionally, the ball seat is fixedly connected with a limiting plate which is provided with a limiting hole, and the nitinol wires pass through the limiting hole and are fixedly connected with the ball seat.

Optionally, the adjusting piece comprises a connecting plate fixedly connected with the swivel, a top end of the connecting plate is fixedly connected with a third hydraulic pump, the third hydraulic pump is electrically connected with the intraoperative adjuster, a top end of the third hydraulic pump is fixedly connected with a connecting frame, a bottom end of the connecting frame is fixedly connected with a moving rod, and a bottom end of the moving rod is hinged with the sleeve.

Optionally, the intraoperative adjuster includes an adjusting housing, which is provided with a distance sensor and a signal emitting device for emitting infrared target radiation, and a control module for controlling the movement of the rotary motor, the first hydraulic pump, the second hydraulic pumps and the third hydraulic pump is arranged in the adjusting housing, and the control module is electrically connected with the distance sensor and the signal emitting device.

Optionally, the brightness adjuster comprises an adjusting base, and adjusting buttons for controlling the brightness of the operating lamp is arranged on the adjusting base.

Optionally, a top end of the telescopic support rod is fixedly connected with a fixing seat.

Optionally, the distance between the operating lamp on the first lighting assembly and the telescopic support rod is not greater than the distance between the operating lamp on the second lighting assembly and the telescopic support rod.

According to the present disclosure, two groups of lighting assemblies, the first lighting assembly and the second lighting assembly, are arranged, and the second lighting assembly moves independently with the first lighting assembly, so that a position angle of the first lighting assembly or the second lighting assembly may be conveniently adjusted according to the actual needs during the operation.

The first adjusting part, the adjusting pieces, the adjusting rods and the second adjusting part are arranged so that the angle of the operating lamps may be adjusted, and the intraoperative adjuster is arranged; and the first infrared and the second infrared sensors are matched with the intraoperative adjuster to realize the position angle of the operating lamps, so that the position angle of the operating lamps does not need to be manually adjusted, and the possibility of contamination in the operation process is reduced.

By setting the intraoperative adjuster, the position and angle of the intraoperative adjuster may be adjusted according to the actual use requirements, so that the intraoperative adjuster is set corresponding to an area to be illuminated, and the operating lamp can change according to the position and angle of the intraoperative adjuster, thus improving the lighting effect of the operating lamp.

By setting the brightness adjuster, the brightness adjuster can adjust the brightness of the operating lamps, and the brightness adjuster is foot-stepped, so that the brightness of the operating lamps may be adjusted only by stepping on the brightness adjuster when the brightness adjuster is in use, with convenience in brightness adjustment of the operating lamps, and reduced possibility of contamination in the brightness adjustment process.

BRIEF DESCRIPTION OF THE DRAWINGS

In order to more clearly explain the embodiments of the present disclosure or the technical solutions in the prior art, the following will briefly introduce the drawings that need to be used in the embodiments. Obviously, the drawings in the following description are only some embodiments of the present disclosure. For those of ordinary skill in the art, other drawings may be obtained according to these drawings without any creative efforts.

DETAILED DESCRIPTION OF THE EMBODIMENTS

Figure 1:
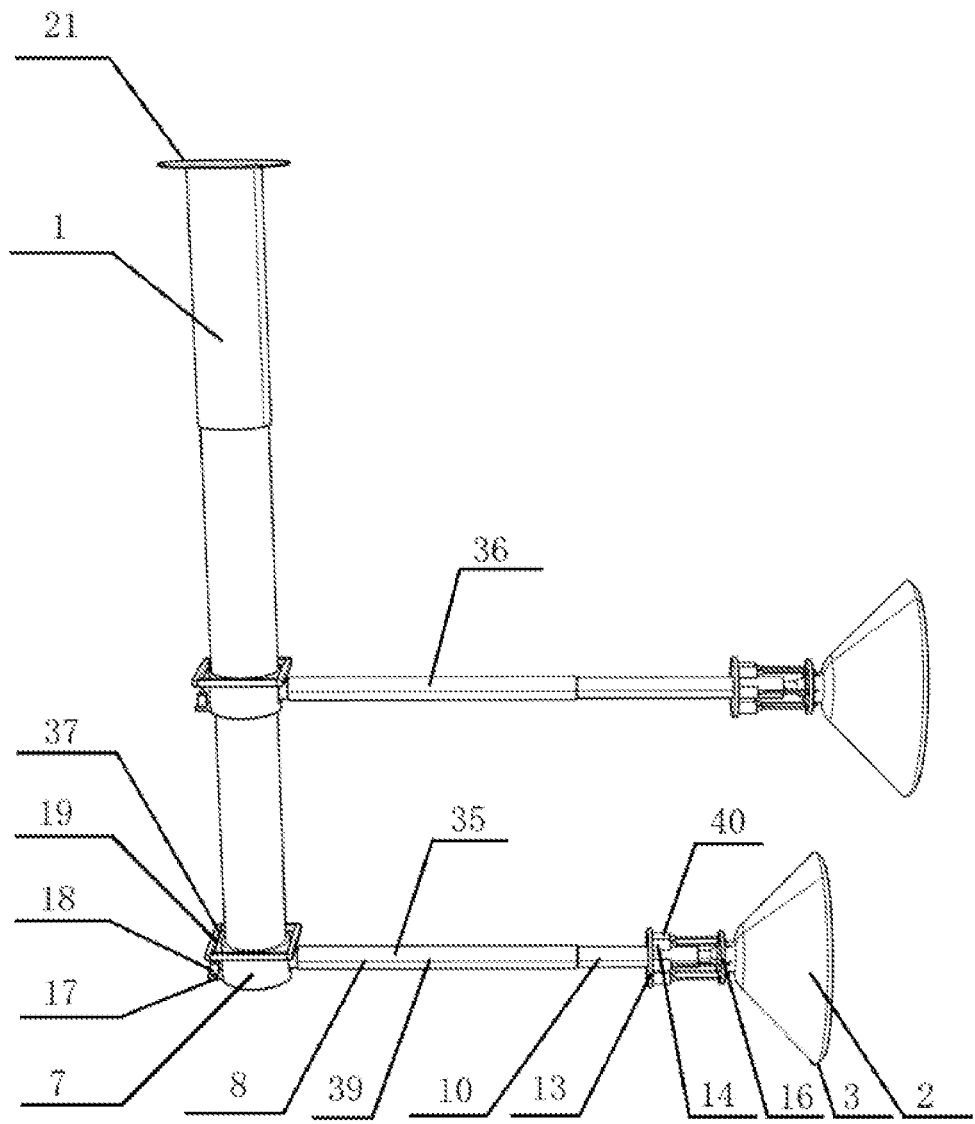
FIG. 1 is a perspective view of an automatically adjustable shadowless operating lamp according to at least one embodiment of the present disclosure.
Figure 2:
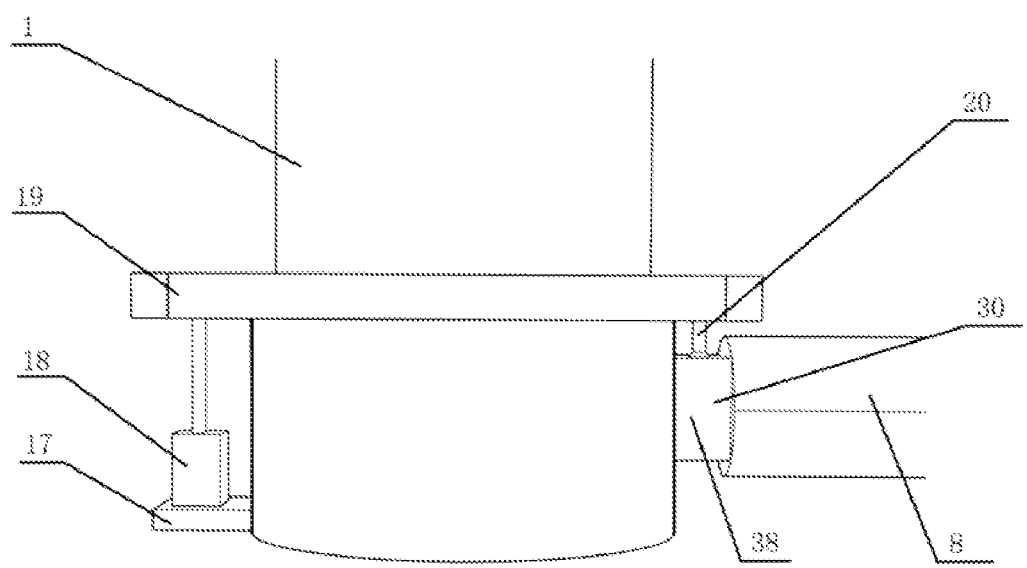
FIG. 2 is a perspective view of a first adjusting part according to at least one embodiment of the present disclosure.
Figure 3:
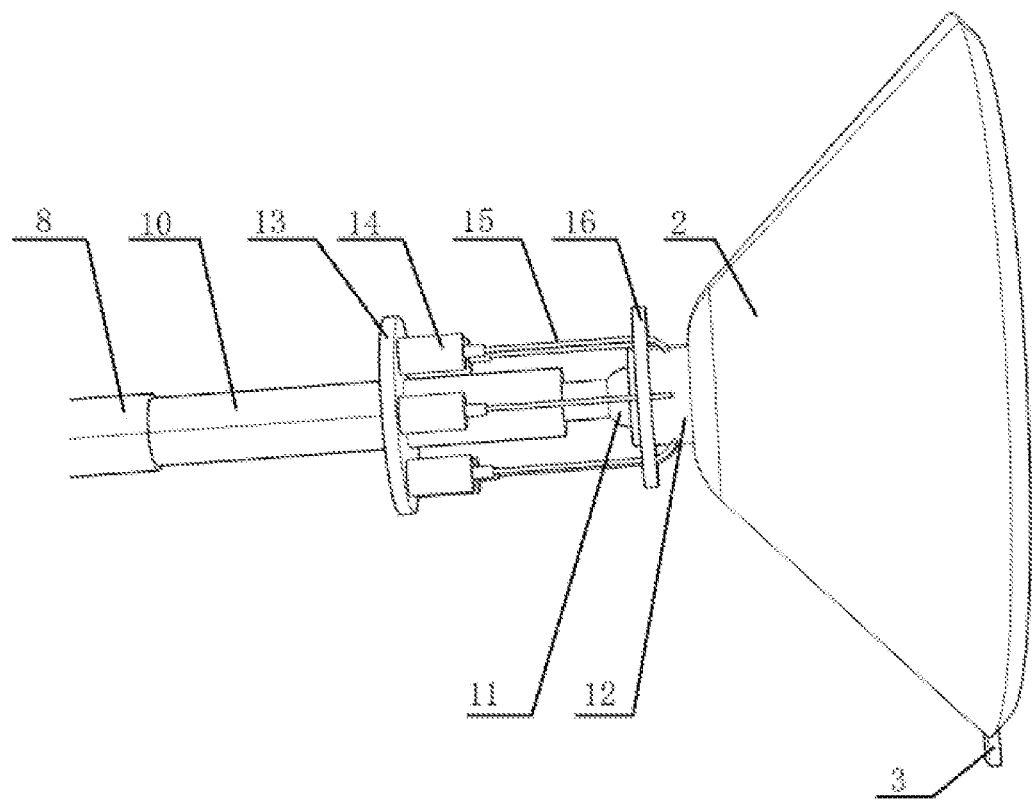
FIG. 3 is a perspective view of a second adjusting part according to at least one embodiment of the present disclosure.
Figure 4:
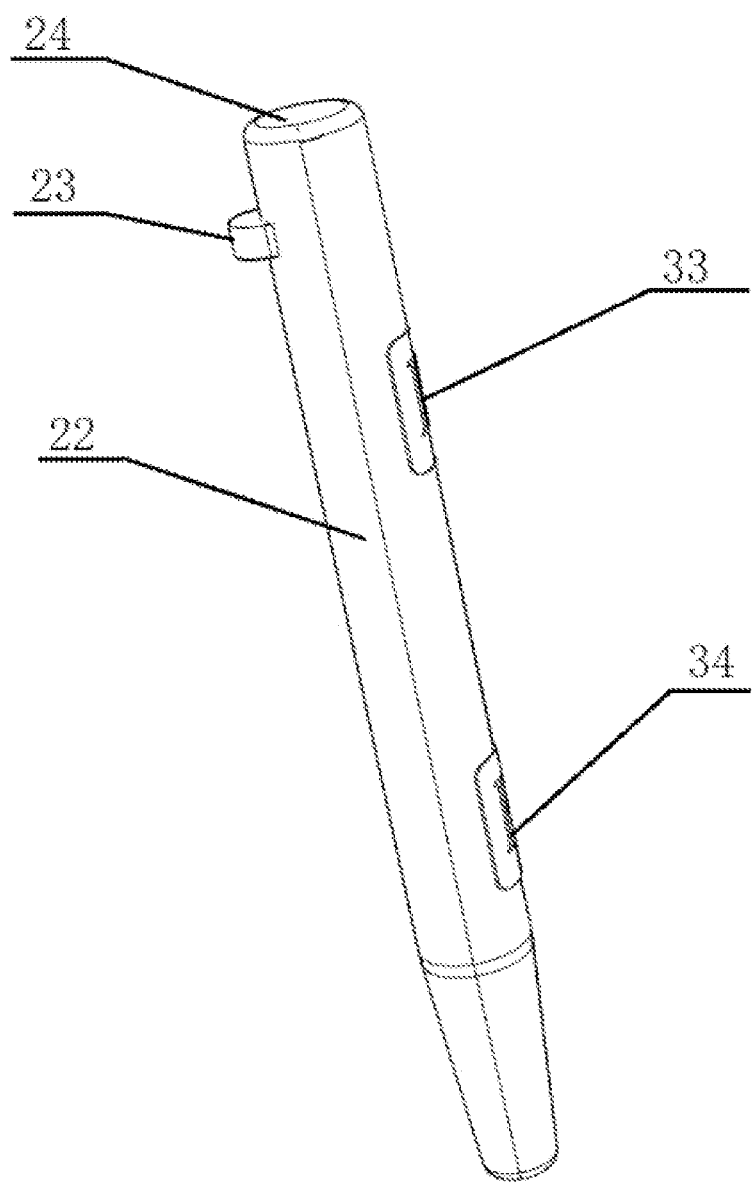
FIG. 4 is a perspective view of an intraoperative adjuster according to at least one embodiment of the present disclosure.
Figure 5:
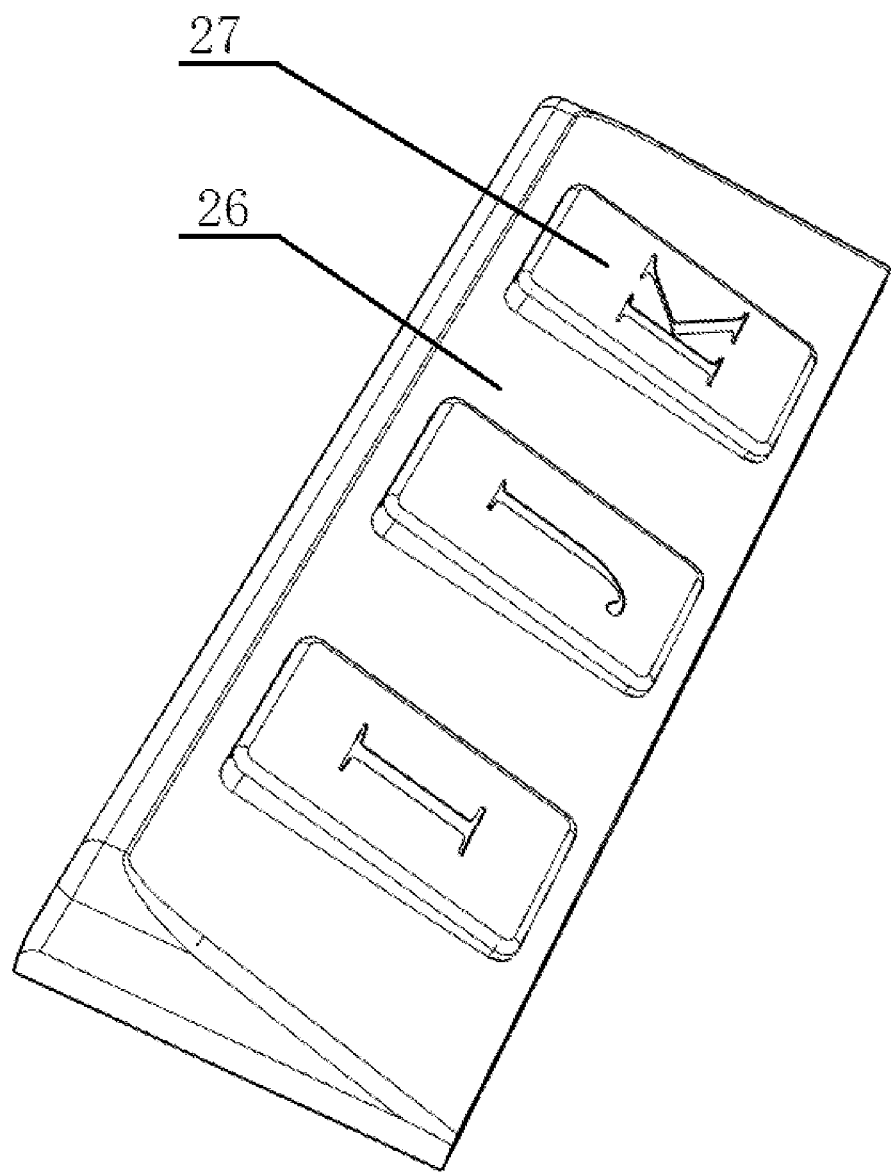
FIG. 5 is a perspective view of a brightness adjuster according to at least one embodiment of the present disclosure.
Figure 6:
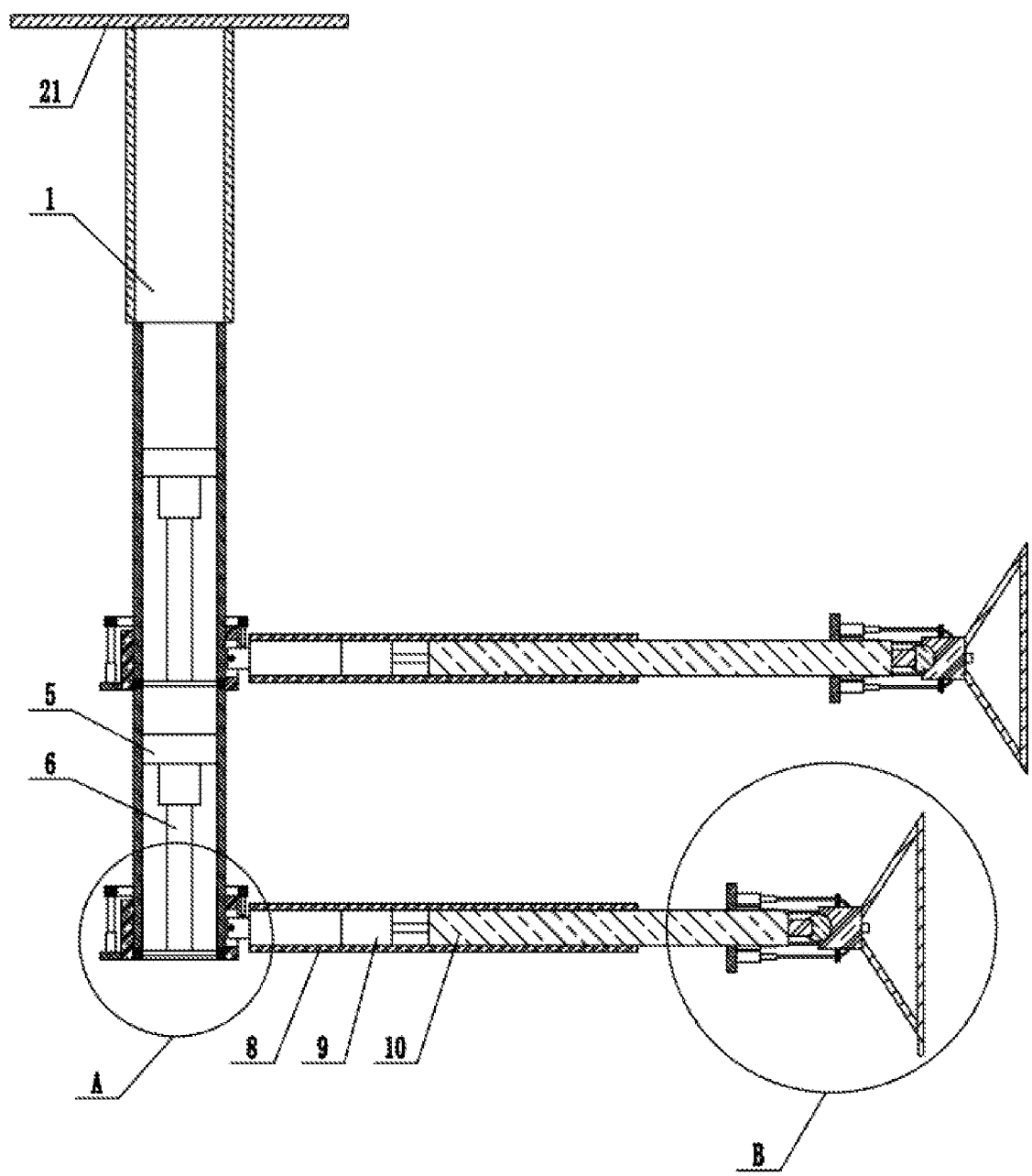
FIG. 6 is a schematic structural diagram of the automatically adjustable shadowless operating lamp according to at least one embodiment of the present disclosure.
Figure 7:
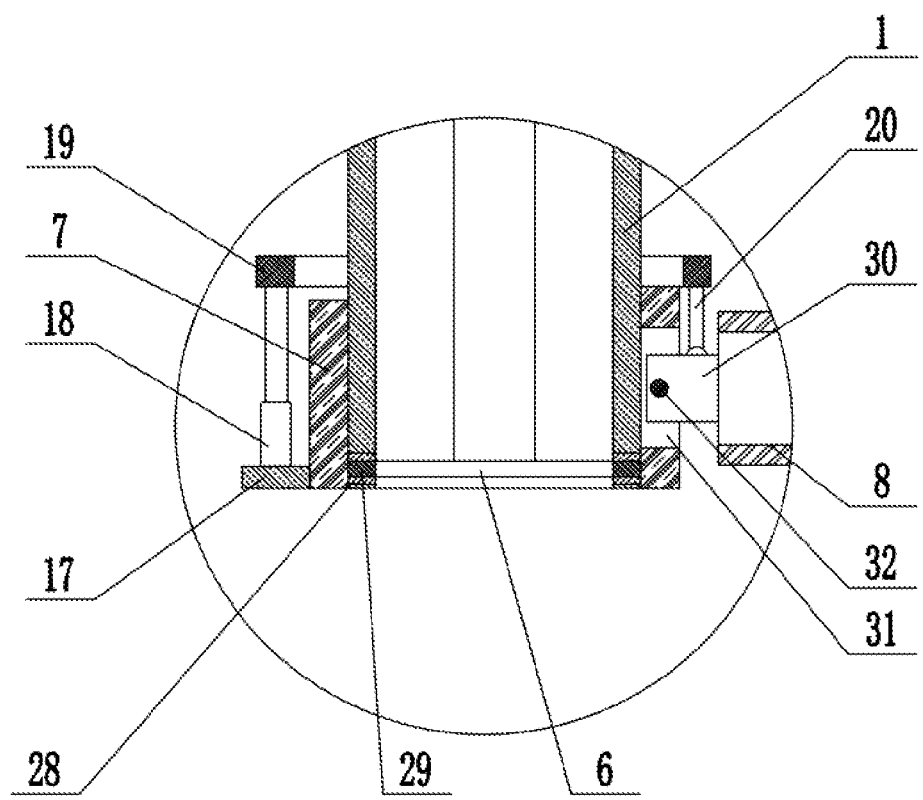
FIG. 7 is a partial enlarged view of A in FIG. 6.
Figure 8:
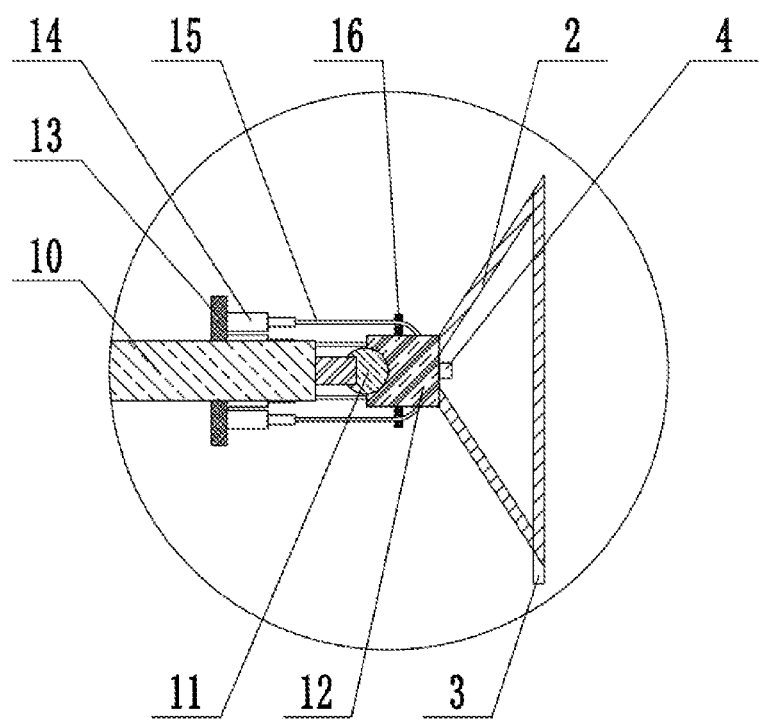
FIG. 8 is a partial enlarged view of B in FIG. 6.
Figure 9:
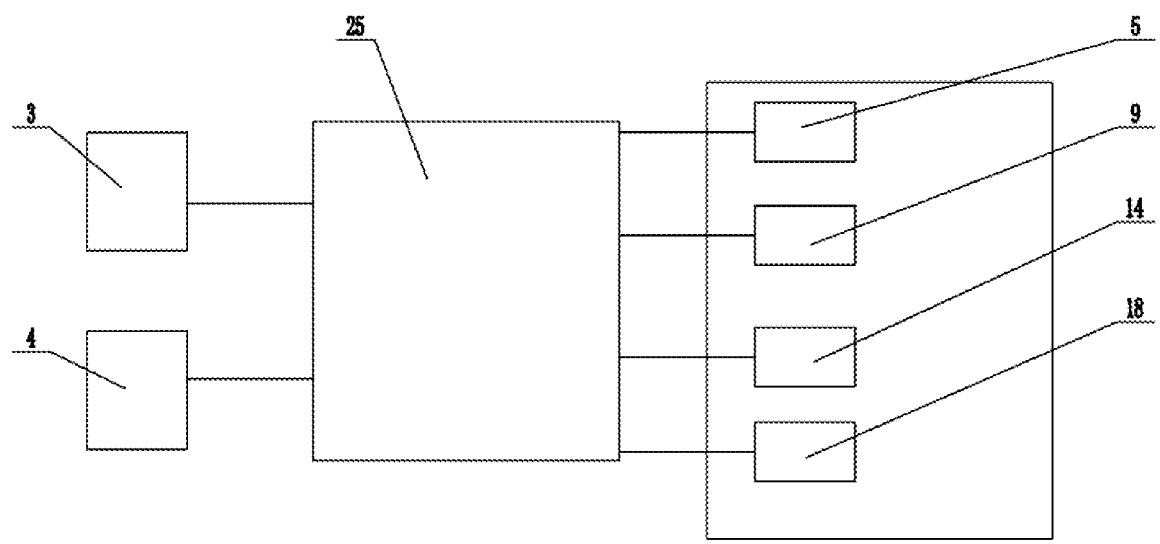
FIG. 9 is a schematic diagram of connection relationship of a control module according to at least one embodiment of the present disclosure.

The technical solutions in the embodiments of the present disclosure will be clearly and completely described below with reference to the drawings in the embodiments of the present disclosure. Obviously, the described embodiments are only part of the embodiments of the present disclosure, but not all of them. Based on the embodiment of the present disclosure, all other embodiments obtained by ordinary technicians in the field without creative labor are within the scope of the present disclosure.

In order to make the above objectives, features and advantages of the present disclosure more obvious and understandable, the present disclosure will be explained in further detail below with reference to the drawings and detailed description.

The present disclosure provides an automatically adjustable shadowless operating lamp. The automatically adjustable shadowless operating lamp comprises a telescopic support rod 1, wherein the telescopic support rod 1 is rotatably connected with a first lighting assembly 35 and a second lighting assembly 36 with a same structure, the second lighting assembly 36 is positioned above the first lighting assembly 35, and the second lighting assembly 36 moves independently with the first lighting assembly 35; the first lighting assembly 35 comprises a first adjusting part 37, the first adjusting part 37 is rotationally connected with the telescopic support rod 1 and is hinged with an adjusting piece 39 through an adjusting piece 38, a tail end of the adjusting piece 39 is fixedly connected with a second adjusting part 40, and the adjusting piece 39 is hinged with an operating lamp 2 through the second adjusting part 40, and the operating lamp 2 is electrically connected with a brightness adjuster arranged below the operating table; a first infrared sensor 3 is arranged at a bottom of the operating lamp 2, a second infrared sensor 4 is arranged in the operating lamp 2, and the first infrared sensor 3, the second infrared sensor 4, the first adjusting part 37, the adjusting piece 39 and the adjusting piece 38 are all electrically connected with an intraoperative adjuster arranged on the operating table.

The second lighting assembly 36 moves independently with the first lighting assembly 35. It may be understood that a driving device contained in the second lighting assembly 36 is also electrically connected with the intraoperative adjuster, and the intraoperative adjuster is also provided with a switch button (not shown in the figure), that is, by controlling the switch button, the intraoperative adjuster can control the first lighting assembly 35 or the second lighting assembly 36 to move, so as to make the two lighting assemblies illuminate at different positions according to the operation requirements. As for the control of the first lighting assembly 35 or the second lighting assembly 36 by switching the switch button, this technology belongs to the prior art, so this present disclosure will not go into too much detail here. The purpose of setting two sets of lighting assemblies is to improve the lighting effect of the operating lamp, and the lighting assemblies are not limited to two sets, and multiple sets may be set according to the actual present disclosure. If multiple sets of lighting assemblies are arranged, the rest of the lighting assemblies should be controlled by the switch button.

The device should be as used as follows: firstly, determining the area to be illuminated during the operation, determining which lighting assembly to use for illuminating, and switching to corresponding lighting assembly through the switch button. Then, placing the intraoperative adjuster vertically. At this time, the distance between the intraoperative adjuster and the telescopic support rod 1 should be smaller than the distance between the operating lamp 2 and the telescopic support rod 1, and the rotation of the first adjusting part 37 drives the adjusting piece 39 and the operating light 2 to rotate 360°. When the adjusting piece 39 is directly above the intraoperative adjuster, the intraoperative adjuster senses the adjusting piece 39 and controls the first adjusting part 37 to stop rotating. At this time, the intraoperative adjuster and the operating lamp 2 are in the same vertical plane, and then the adjusting piece 39 moves to drive the operating lamp 2 to contract. As the bottom end of the operating lamp 2 is provided with the first infrared sensor 3, the infrared signal emitted by the intraoperative adjuster is sensed by the first infrared sensor 3. and fed back to the intraoperative adjuster, which controls the adjusting piece 39 to stop moving. At this time, the operating lamp 2 is located right above the intraoperative adjuster, and then an angle of the intraoperative adjuster is adjusted according to the specific intended illumination angle. After the angle adjustment of the intraoperative adjuster is finished, the second adjusting part 40 is started to make the operating lamp 2 rotate, and the second infrared sensor 4 on the operating lamp 2 senses the signal sent by the intraoperative adjuster and feeds back to the intraoperative adjuster. The intraoperative adjuster controls the second adjusting part 40 to stop moving. At this time, the intraoperative adjuster and the infrared sensor 4 should be on the same straight line, and the infrared sensor 4 may be arranged at the center of the operating lamp 2, thus improving the lighting effect of the operating lamp 2 on the area to be illuminated.

The intraoperative adjuster may be hand-held by the operator in the process of use, and the position and angle thereof may be adjusted according to the actual needs. During an operation, the brightness of the operating lamp 2 may be adjusted by adjusting the brightness adjuster according to the actual needs.

In a further optimization scheme, the first adjusting part 37 comprises a rotary motor 5 arranged in the telescopic support rod 1, the rotary motor 5 is electrically connected with the intraoperative adjuster, an output end of the rotary motor 5 is fixedly connected with a connecting rod 6, and the telescopic support rod 1 is externally sleeved with a swivel 7 which is hinged with the adjusting piece 39, and the swivel 7 is fixedly connected with the connecting rod 6 through a bearing. The bearing comprises two annular plates 28 which are oppositely arranged, the annular plates 28 are fixedly connected with the telescopic support rod 1, a rotating ring 29 is arranged between the two annular plates 28, and the rotating ring 29 is fixedly connected with the connecting rod 6 and the swivel 7. The motor 5 drives the connecting rod 6 to rotate, and the swivel 7 to rotate through the rotating ring 29, so as to drive the operating lamp 2 to rotate 360°, which is convenient for the next operation.

In a further optimization scheme, the adjusting piece 39 comprises a sleeve 8 hinged with the swivel 7, and a first hydraulic pump 9 and a long rod 10 are arranged in the sleeve 8. The first hydraulic pump 9 is electrically connected with the intraoperative adjuster, and the long rod 10 is telescoped in the sleeve 8 through the first hydraulic pump 9. A tail end of the long rod 10 is fixedly connected with a ball 11, and the bottom end of the operating lamp 2 is fixedly connected with a ball seat 12 matched with the ball 11.

The first hydraulic pump 9 pushes the long rod 10, so that the long rod 10 can expand and contract. The ball 11 is arranged at the tail end of the long rod 10, and the ball seat 12 matched with the ball 11 is arranged on the operating lamp 2. The ball 11 is located in a spherical groove (not shown in the figure) on the ball seat 12, so that the operating lamp 2 can rotate by 270°, which is convenient for the operating lamp 2 to illuminate the area to be illuminated.

One end of the sleeve 8 close to the telescopic support rod 1 is fixedly connected with a rotating plate 30, a groove 31 is formed in the swivel 7, the rotating plate 30 is located in the groove 31, and the rotating plate 30 is rotationally connected with the swivel 7 through a rotating rod 32. With the cooperation of the rotating plate 30 and the rotating rod 32, the sleeve 8 can be adjusted up and down by 15° to 30°. Because the operating lamp 2 may have a blind area in the angle adjustment process, the rotating plate 30 and the rotating rod 32 are arranged, so that the adjusting angle of the operating lamp 2 is enlarged, which makes it more suitable for the operating environment, and has high practicability.

In a further optimization scheme, the second adjusting part 40 includes a supporting plate 13 fixedly connected with the long rod 10, and a plurality of second hydraulic pumps 14 are circumferentially fixedly connected to one side of the supporting plate 13 close to the operating lamp 2, and all the second hydraulic pumps 14 are electrically connected with the intraoperative adjuster, and the movable ends of the second hydraulic pumps 14 are fixedly connected with the ball seat 12 through nitinol wires 15. A plurality of second hydraulic pumps 14 are arranged on the supporting plate 13 on the long rod 10. Because the operating lamp 2 can rotate by 270°, in order to control the rotation of the operating lamp 2, a plurality of second hydraulic pumps 14 are arranged. Through the contraction or relaxation of different second hydraulic pumps 14, the nitinol wires 15 fixedly connected with the second hydraulic pumps 14 drive the operating lamp 2 to rotate. At the same time, because the operating lamp 2 rotates, the second infrared sensor 4 located in the operating lamp 2 also rotates correspondingly, and the operating lamp 2 is usually located above the operating table. Therefore, when the operating lamp 2 rotates, the second hydraulic pump 14 located at the lower position contracts, and the second hydraulic pump 14 located at the higher position does not move or relax according to the actual situation, so that the operating lamp 2 rotates downward. During the downward rotation of the operating lamp 2, the second infrared sensor 4 senses the signal sent by the intraoperative adjuster to complete the angle adjustment step of the operating lamp 2.

In the further optimization scheme, the ball seat 12 is fixedly connected with a limiting plate 16, the limiting plate 16 is provided with a limiting hole, and the nitinol wires 15 pass through the limiting hole and are fixedly connected with the ball seat 12. Since there are a plurality of second hydraulic pumps 14, there are a plurality of nitinol wires 15. In order to avoid the winding of the plurality of nitinol wires 15 due to movement, the limiting plate 16 and the limiting hole on the limiting plate 16 enlarge the distance between adjacent nitinol wires 15 and prolong the service life of the device.

In a further optimization scheme, the adjusting piece 38 includes a connecting plate 17 fixedly connected with the swivel 7, a top of the connecting 17 is fixedly connected with a third hydraulic pump 18, the third hydraulic pump is electrically connected with the intraoperative adjuster, a top of the third hydraulic pump is fixedly connected with a connecting frame 19, a bottom of the connecting frame is fixedly connected with a moving rod 20, and a bottom of the moving rod is hinged with the sleeve 8. In order to control the up-and-down adjustment of the sleeve 8 by 15° to 30°, the third hydraulic pump 18 is provided, and the third hydraulic pump 18 moves to drive the connecting frame 19 to move. The connecting frame 19 is sleeved outside the telescopic support rod 1, which does not affect the normal work of the telescopic support rod 1 and the swivel 7. The moving rod 20 on the connecting frame 19 is hinged with the rotating plate 30, thus achieving the hinge effect with the sleeve 8, and the angle of the sleeve 8 is changed in the up-and-down direction by controlling the position change of the moving rod 20. The adjustment piece should be used after the second adjusting part 40 works. If the second infrared sensor 4 does not sense the intraoperative adjuster after the operating lamp 2 rotates during the operation of the second adjusting part 40, the intraoperative adjuster controls the third hydraulic pump 18 to work, so that the sleeve 8 drives the angle of the operating lamp 2 to change. Then, the second adjusting part 40 works again and senses the intraoperative adjuster again until the intraoperative adjuster is sensed.

In a further optimization scheme, the intraoperative adjuster includes an adjusting housing 22, and the adjusting housing 22 is provided with a distance sensor 23 and a signal emitting device 24 for emitting infrared target radiation. A control module 25 for controlling the movement of the rotary motor 5, the first hydraulic pump 9, the second hydraulic pumps 14 and the third hydraulic pump 18 is arranged in the adjusting housing 22, and the control module 25 is electrically connected with the distance sensor 23 and the signal emitting device 24.

The adjusting housing 22 is provided with a first start button 33 and a second start button 34, both the first start button 33 and the second start button 34 are electrically connected with the control module 25. When the adjustment is started in operation, the first start button 33 is pressed, the distance sensor 23 works, and the rotary motor 5 rotates to drive the sleeve 8 and the long rod 10 to rotate. When the sleeve 8 and the long rod 10 rotate above the distance sensor 23, the distance sensor 23 senses and feeds back to the control module 25, the control module 25 controls the rotary motor to stop working.

Then, the control module 25 controls the first hydraulic pump 9 and the signal emitting device 24 to start, and the first hydraulic pump 9 drives the long rod 10 to contract until the first infrared sensor 3 senses the signal emitted by the signal emitting device 24. The first infrared sensor 3 feeds back to the control module 25, which controls the first hydraulic pump 9 to stop working, then the second start button 34 is pressed, the second start button 34 controls the second infrared sensor 4, multiple second hydraulic pumps 14 and the signal emitting device 24 to start, and the operating lamp 2 rotates. When the second infrared sensor 4 senses the signal sent by the signal emitting device 24, the second infrared sensor 4 feeds back to the control module 25 and the control module 25 controls multiple second hydraulic pumps 14 to stop working. If the second infrared sensor 4 does not sense the signal emitting device 24 after the operating lamp 2 rotates for one cycle, the second infrared sensor 4 fed back to the control module 25. The control module 25 controls the third hydraulic pump 18 to work, and after the sleeve 8 rotates for a certain angle, it re-controls multiple second hydraulic pumps 14 to rotate one cycle again until the second infrared sensor 4 senses the signal from the signal emitting device 24.

In the above process, multiple second hydraulic pumps 14 control the operating lamp 2 to rotate one cycle, and the second infrared sensor 4 senses the signal emitting device 24, so that the operating lamp 2 and the adjusting housing 22 are on the same straight line, which belongs to the conventional technology and will not be repeated here.

In a further optimization scheme, the brightness adjuster comprises an adjusting base 26, and adjusting buttons 27 for controlling the brightness of the operating lamp 2 is arranged on the adjusting base 26. The adjusting base 26 may be fixedly connected to the ground below the operating table. When the brightness of the operating lamp 2 needs to be adjusted, it is only necessary to step on different adjusting buttons 27, which is convenient to use and not easy to pollute the operation. As there are two lighting assemblies, in order to realize the brightness of the operating lamps 2 in different lighting assemblies, the brightness adjuster may also be provided with a switch button (not shown in the figure), through which the brightness of the operating lamps 2 in different lighting assemblies may be controlled. The working principle of the brightness adjustment is the same as that of the intraoperative adjuster controlling the movement of the lighting assemblies, and the brightness of the operating lamps 2 in different lighting assemblies can be adjusted by only one brightness adjuster, which is convenient to adjust, and the brightness adjuster does not occupy too much space, so it has high practicability.

In a further optimization scheme, the top of the telescopic support rod 1 is fixedly connected with a fixing seat 21. The fixing seat 21 is where the telescopic support rod 1 is connected with the roof of the operating room and serves as a fixing device. The telescopic support rod 1 has a telescopic structure, so a driving device (not shown in the figure) can be arranged on the telescopic support rod 1 according to the actual use requirements to achieve the effect of adjusting the height of the operating lamp during the operation.

In a further optimization scheme, the distance between the operating lamp 2 on the first lighting assembly 35 and the telescopic support rod 1 is not greater than the distance between the operating lamp 2 on the second lighting assembly 36 and the telescopic support rod 1. Because the first lighting assembly 35 and the second lighting assembly 36 are on the same vertical plane, in order to ensure that the first lighting assembly 35 does not affect the lighting effect of the second lighting assembly 36, the operating lamps 2 on the first lighting assembly 35 and the second lighting assembly 36 are in a misalignment state, and because the first lighting assembly 35 and the second lighting assembly 36 move independently, the operating lamps 2 on the two lighting assemblies are always in a misalignment state, thus improving the lighting effect of the operating lamps 2.

Working principle: before operation, the height of the telescopic support rod 1 is adjusted. During operation, the area to be illuminated is firstly determined, and the switch button is utilized to switch to the first lighting assembly 35 or the second lighting assembly 36. Then, the adjusting housing 22 is placed vertically, the first start button 33 is pressed, and the distance sensor 23 works. The rotary motor 5 rotates to drive the sleeve 8 and the long rod 10 to rotate. When the sleeve 8 and the long rod 10 rotate above the distance sensor 23, the distance sensor 23 senses and feeds back to the control module 25, and the control module 25 controls the rotary motor 5 to stop working. Then, the control module 25 controls the first hydraulic pump 9 and the signal emitting device 24 to start, and the first hydraulic pump 9 drives the long rod 10 to contract. When the first infrared sensor 3 senses the signal from the signal emitting device 24, the first infrared sensor 3 feeds back to the control module 25. The control module 25 controls the first hydraulic pump 9 to stop working, controls the angle of the adjusting housing 22, so that the adjusting housing 22 corresponds to the area to be illuminated, and then the second start button 34 is pressed, the second start button 34 controls the second infrared sensor 4, a plurality of second hydraulic pumps 14 and the signal emitting device 24 to start, and the operating lamp 2 rotates. When the second infrared sensor 4 senses the signal sent by the signal emitting device 24, the second infrared sensor 4 feeds back to the control module 25, which controls multiple second hydraulic pumps 14 to stop working. If the second infrared sensor 4 fails to sense the signal emitting device 24 after the operating lamp 2 rotates one cycle, the second infrared sensor 4 feeds back to the control module 25, the control module 25 controls the third hydraulic pump 18 to work, and after the sleeve 8 rotates for a certain angle, the control module 25 controls multiple second hydraulic pumps 14 to rotate one cycle again until the second infrared sensor 4 senses the signal emitted by the signal emitting device 24.

In the description of the present disclosure, it should be understood that the orientation or positional relationship indicated by terms "longitudinal", "transverse", "upper", "lower", "front", "rear", "left", "right", "vertical", "horizontal", "top", "bottom", "inner", "outer", etc. is based on the orientation or positional relationship shown in the drawings, and is only for the convenience of describing the present disclosure, rather than indicating or implying that the device or element referred to must have a particular orientation, be constructed and operate in a particular orientation, and therefore should not be understood as limiting the disclosure.

The above-mentioned embodiments only describe the preferred mode of the present disclosure, but do not limit the scope of the present disclosure. On the premise of not departing from the design spirit of the present disclosure, all kinds of modifications and improvements made by ordinary technicians in the field to the technical scheme of the present disclosure shall fall within the scope of protection determined by the claims of the present disclosure.

What is claimed is:

1. An automatically adjustable shadowless operating lamp, comprising a telescopic support rod, wherein the telescopic support rod is rotatably connected with a first lighting assembly and a second lighting assembly with a same structure, the second lighting assembly is positioned above the first lighting assembly, and the second lighting assembly moves independently with the first lighting assembly;

the first lighting assembly comprises a first adjusting part, the first adjusting part is rotationally connected with the telescopic support rod and is hinged with an adjusting rod through an adjusting piece, and a tail end of the adjusting rod is fixedly connected with a second adjusting part, and the adjusting rod is hinged with an operating lamp through the second adjusting part, and the operating lamp is electrically connected with a brightness adjuster arranged below an operating table;

a first infrared sensor is arranged at a bottom of the operating lamp, a second infrared sensor is arranged in the operating lamp, and the first infrared sensor, the second infrared sensor, the first adjusting part, the adjusting rod and the adjusting piece are all electrically connected with an intraoperative adjuster arranged on the operating table;

the first adjusting part comprises a rotary motor arranged in the telescopic support rod, the rotary motor is electrically connected with the intraoperative adjuster, an output end of the rotary motor is fixedly connected with a connecting rod, and the telescopic support rod is externally sleeved with a swivel hinged with the adjusting rod, and the swivel is fixedly connected with the connecting rod through a bearing;

the adjusting rod comprises a sleeve hinged with the swivel, a first hydraulic pump and a long rod are arranged in the sleeve, the first hydraulic pump is electrically connected with the intraoperative adjuster, the long rod is telescoped in the sleeve through the first hydraulic pump, a tail end of the long rod is fixedly connected with a ball, and the bottom end of the operating lamp is fixedly connected with a ball seat which is matched with the ball;

the second adjusting part comprises a supporting plate fixedly connected with the long rod, and a plurality of second hydraulic pumps are circumferentially fixedly connected to one side of the supporting plate close to the operating lamp, and all the second hydraulic pumps are electrically connected with the intraoperative adjuster, and movable ends of the second hydraulic pumps are fixedly connected with the ball seat through nitinol wires;

the adjusting piece comprises a connecting plate fixedly connected with the swivel, a top end of the connecting plate is fixedly connected with a third hydraulic pump, the third hydraulic pump is electrically connected with the intraoperative adjuster, a top end of the third hydraulic pump is fixedly connected with a connecting frame, a bottom end of the connecting frame is fixedly connected with a moving rod, and a bottom end of the moving rod is hinged with the sleeve.

2. The automatically adjustable shadowless operating lamp according to claim 1, wherein the ball seat is fixedly connected with a limiting plate which is provided with a limiting hole, and nitinol wires pass through the limiting hole and are fixedly connected with the ball seat.

3. The automatically adjustable shadowless operating lamp according to claim 2, wherein the intraoperative adjuster comprises an adjusting housing, the adjusting housing is provided with a distance sensor and a signal emitting device for emitting infrared target radiation, and a control module for controlling the movement of the rotary motor, the first hydraulic pump, the second hydraulic pumps and the third hydraulic pump is arranged in the adjusting housing, and the control module is electrically connected with the distance sensor and the signal emitting device.

4. The automatically adjustable shadowless operating lamp according to claim 1, wherein the brightness adjuster comprises an adjusting base, and adjusting buttons for controlling the brightness of the operating lamp is arranged on the adjusting base.

5. The automatically adjustable shadowless operating lamp according to claim 1, wherein a top end of the telescopic support rod is fixedly connected with a fixing seat.

6. The automatically adjustable shadowless operating lamp according to claim 1, wherein a distance between the operating lamp on the first lighting assembly and the telescopic support rod is not larger than a distance between the operating lamp on the second lighting assembly and the telescopic support rod.

* * * * *